(12) United States Patent
Wu

(10) Patent No.: US 11,156,332 B2
(45) Date of Patent: Oct. 26, 2021

(54) ELECTRIC SCENTED CANDLE

(71) Applicant: AE TECHNOLOGIES CO., LTD., Guangdong (CN)

(72) Inventor: Wenfeng Wu, Guangdong (CN)

(73) Assignee: AE TECHNOLOGIES CO., LTD., Guangzhou (CN)

( * ) Notice: Subject to any disclaimer, the term of this patent is extended or adjusted under 35 U.S.C. 154(b) by 195 days.

(21) Appl. No.: 16/605,500

(22) PCT Filed: Aug. 30, 2019

(86) PCT No.: PCT/CN2019/103710
§ 371 (c)(1),
(2) Date: Oct. 15, 2019

(87) PCT Pub. No.: WO2021/035688
PCT Pub. Date: Mar. 4, 2021

(65) Prior Publication Data
US 2021/0247042 A1    Aug. 12, 2021

(51) Int. Cl.
*F21S 10/04* (2006.01)
*A61L 9/03* (2006.01)
*F21S 9/02* (2006.01)

(52) U.S. Cl.
CPC ............. *F21S 10/043* (2013.01); *A61L 9/032* (2013.01); *F21S 9/02* (2013.01); *A61L 2209/111* (2013.01)

(58) Field of Classification Search
CPC . F21S 10/043; F21S 9/02; F21S 10/04; F21V 35/00; F21V 35/003; A61L 9/032; A61L 2209/111
See application file for complete search history.

(56) References Cited

U.S. PATENT DOCUMENTS 7,133,605 B2 * 11/2006 Niemeyer ................ A61L 9/03
                                                   392/390
7,670,035 B2 *  3/2010 Tsai ..................... F21S 9/02
                                                   362/392
(Continued)

FOREIGN PATENT DOCUMENTS

| CN | 203571587 U | 4/2014 |
| CN | 105258070 A | 1/2016 |
| CN | 107461712 A | 12/2017 |

OTHER PUBLICATIONS

English Machine Translation of CN 203571587 provided by ESPACENET (Year: 2014).*

*Primary Examiner* — Zheng Song

(57) ABSTRACT

The invention relates to the field of illumination technology and provides an electric scented candle, which comprises the base, the hollow filled body having two ends respectively formed with the opening, the fragrance assembly and the candle tip, wherein the fragrance assembly is arranged in the receiving cavity of the base, the fragrance assembly comprises the solid perfume and the heating mechanism for heating the solid perfume, the base is detachably connected with the filled body, the holding plate is arranged in the filled body, and the candle tip is arranged in the filled body and extends through the though-hole to a position above the holding plate. Real burning flames can be simulated by the candle tip, and wax surface of real burning candles adjacent to the candle tip can be simulated by the layer of paraffin arranged on the holding plate, providing better simulation effect of the scented candle.

18 Claims, 3 Drawing Sheets

(56) References Cited

U.S. PATENT DOCUMENTS

| | | | |
|---|---|---|---|
| 9,585,980 B1* | 3/2017 | Li | F21S 6/001 |
| 2008/0036332 A1* | 2/2008 | Helf | B06B 1/0238 |
| | | | 310/311 |
| 2014/0140042 A1* | 5/2014 | Schreiber | A61L 9/037 |
| | | | 362/96 |
| 2016/0298816 A1* | 10/2016 | Fang | F21S 10/046 |

* cited by examiner

ELECTRIC SCENTED CANDLE

FIELD OF THE INVENTION

The present invention relates to the field of illumination technology, more particularly to an electric scented candle.

BACKGROUND OF THE INVENTION

Conventional scented candles can be burned to emit fragrance, thereby diffusing fragrance in home to create a certain atmosphere. When a conventional scented candle burns, the wax is constantly consumed and is not reusable, and harmful gases may be generated.

As technology develops rapidly, electric scented candles which can simulate the burning flame and meanwhile meet safety and environmental protection requirements take the place of conventional scented candles and are widely used. In order to produce fragrant vapor in some specific applications, usually the electric scented candles are provided with essential oil. However, due to the intrinsic characteristics of the essential oil, it may volatilize and cause the waste of resources. Furthermore, it is not easy to refill the essential oil for conventional scented candles and the essential oil may leak out. The present invention uses solid perfume heating method, emits fragrance uniformly and durably, simulates the wax surfaces of real burning candles by the simulated flame, and has better simulation effect.

SUMMARY OF THE INVENTION

The present invention aims to solve technical problems of effectively controlling the production of fragrant vapors and producing various fragrances. It avoids the waste of resources and meanwhile provides good simulation effect of the candle lamp.

In order to solve the above technical problems, the present invention provides an electric scented candle, which comprises a base, a hollow filled body having two ends respectively formed with an opening, a fragrance assembly, and a candle tip, wherein a lower end of the filled body is detachably connected with the base, a holding plate is arranged in the filled body, a layer of paraffin is arranged on an upper side of the holding plate, the holding plate is arranged adjacent to an upper opening of the filled body and is provided with a though-hole, and the candle tip is arranged in the filled body and extends through the though-hole to a position above the holding plate;

The base is provided with a receiving cavity for accommodating the fragrance assembly, and the fragrance assembly comprises a solid perfume and a heating mechanism for heating the solid perfume.

Furthermore, an upper side surface of the layer of paraffin preferably may be aligned with an upper end surface of the filled body or is recessed downwards along the filled body.

Furthermore, the upper side surface of the layer of paraffin preferably may be formed as a planar surface, or a recessed surface, or a corrugated surface.

Furthermore, the heating mechanism preferably may comprise a heating ring arranged in the receiving cavity and a first control circuit for controlling the heating of the heating ring, and the solid perfume is arranged in the heating ring.

Furthermore, the heating mechanism preferably may comprise a thermal insulation layer arranged between an inner wall of the receiving cavity and the heating ring.

Furthermore, the solid perfume preferably may be provided with a diffusing hole.

Furthermore, the solid perfume preferably may be provided with a plurality of diffusing holes which form honeycombed or quincunx arrangement.

Furthermore, the solid perfume preferably may be any of fragrant stick, fragrant slice, and fragrant bead.

Furthermore, an upper cap preferably may be removably arranged at an upper end of the receiving cavity, and the upper cap may be provided with a plurality of first air holes.

Furthermore, a bottom cap preferably may be removably arranged at a lower end of the receiving cavity, and the bottom cap may be provided with a plurality of second air holes.

Furthermore, a plurality of third air holes in communication with an interior of the filled body preferably may be provided on a side wall of the base.

Furthermore, an airflow generation device for accelerating air circulation preferably may be arranged above the receiving cavity.

Furthermore, the airflow generation device preferably may comprise a housing and an air outlet body, a plurality of connecting pins are arranged at an upper end of the upper cap, and the housing is connected with the connecting pins.

Furthermore, the holding plate and the filled body preferably may be integrally formed, and the filled body may be made of any of glass, plastic, paraffin, metal, and wood.

Furthermore, the filled body preferably may be oval shaped, straight cylinder shaped, or trapezoid shaped.

Furthermore, the candle tip preferably may comprise a light source, a flame holder, a semitransparent flame cover, and a second control circuit for controlling luminance and/or flicker frequency of the light source, wherein an upper end of the flame holder extends through the though-hole to a position above the holding plate and is arranged with a flame base, a lower end of the flame cover is connected with the flame base, the light source is arranged in the flame base in such a manner that a light emitted by the light source can be projected through a reflecting chamber of the flame cover.

Furthermore, the base preferably may be arranged with a battery compartment for accommodating a battery.

Furthermore, an indicator light preferably may be arranged on a side wall of the base.

Furthermore, the electric scented candle preferably may comprise an inner cover, the inner cover is connected with the base from above, and the filled body covers the inner cover from outside and is connected with the base.

Furthermore, the electric scented candle preferably may comprise a fixing base, a swing support mechanism arranged in the fixing base, and a swing driving mechanism for driving the flame holder to swing around the swing support mechanism, wherein the swing support mechanism is arranged with a swing convex point, the flame holder is provided at its centre of gravity with a swing concave point by which it can be hung on the swing convex point, and the swing driving mechanism comprises a magnet arranged at a lower end of the flame holder and an electromagnetic coil arranged at a bottom of the fixing base.

Compared with the existing technologies, the electric scented candle according to the embodiments of the present invention has advantages as follows.

The electric scented candle according to the embodiments of the present invention comprises the base, the hollow filled body having two ends respectively formed with the opening, the fragrance assembly and the candle tip, wherein the fragrance assembly is arranged in the receiving cavity of the base. In particular, the fragrance assembly comprises the solid perfume and the heating mechanism for heating the solid perfume. By means of the heating mechanism for heating, the fragrance can be diffused uniformly. Due to the solid-state solid perfume, the volatilization of the solid perfume can be significantly reduced, thereby saving resources. Furthermore, since the base is detachably connected with the filled body, it is convenient to replace the solid perfume and maintain internal parts of the scented candle. Meanwhile, since the holding plate is arranged in the filled body and the candle tip is arranged in the filled body and extends through the though-hole to a position above the holding plate, real burning flames can be simulated by the candle tip, and wax surface of real burning candles adjacent to the candle tip can be simulated by the layer of paraffin arranged on the holding plate, thereby providing better simulation effect of the scented candle.

Figure 1:
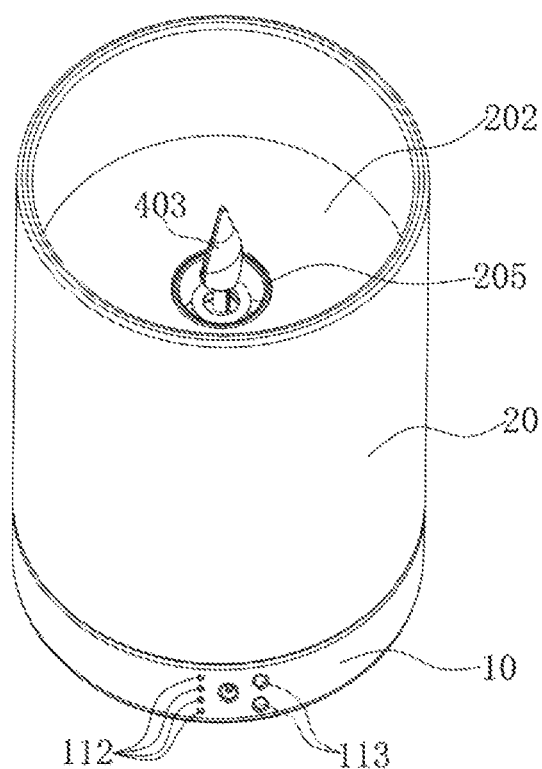
FIG. 1 is a schematic perspective view of an electric scented candle according to an embodiment of the present invention.
Figure 2:
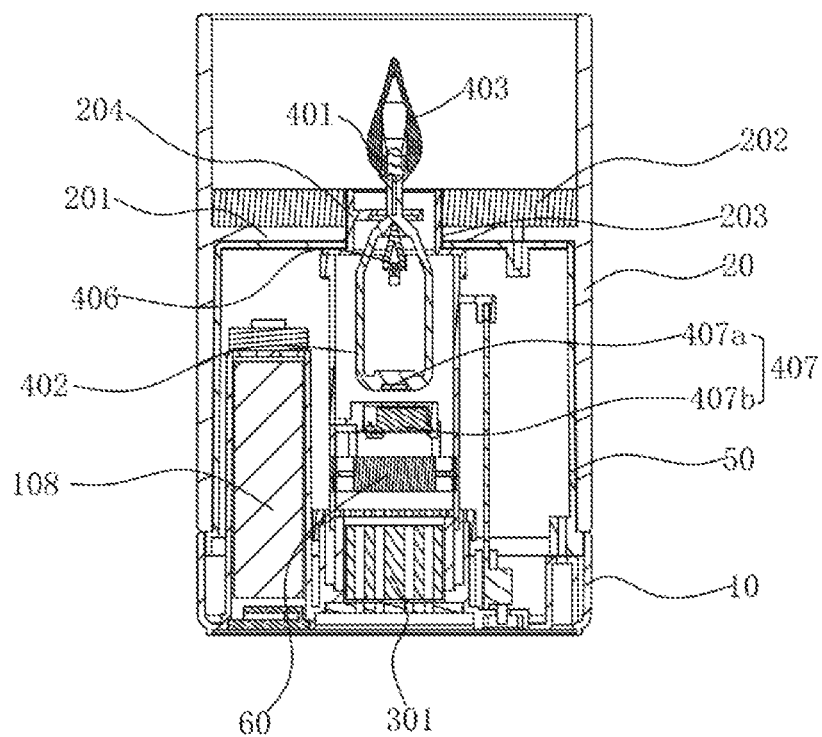
FIG. 2 is a schematic sectional view of an electric scented candle according to an embodiment of the present invention.
Figure 3:
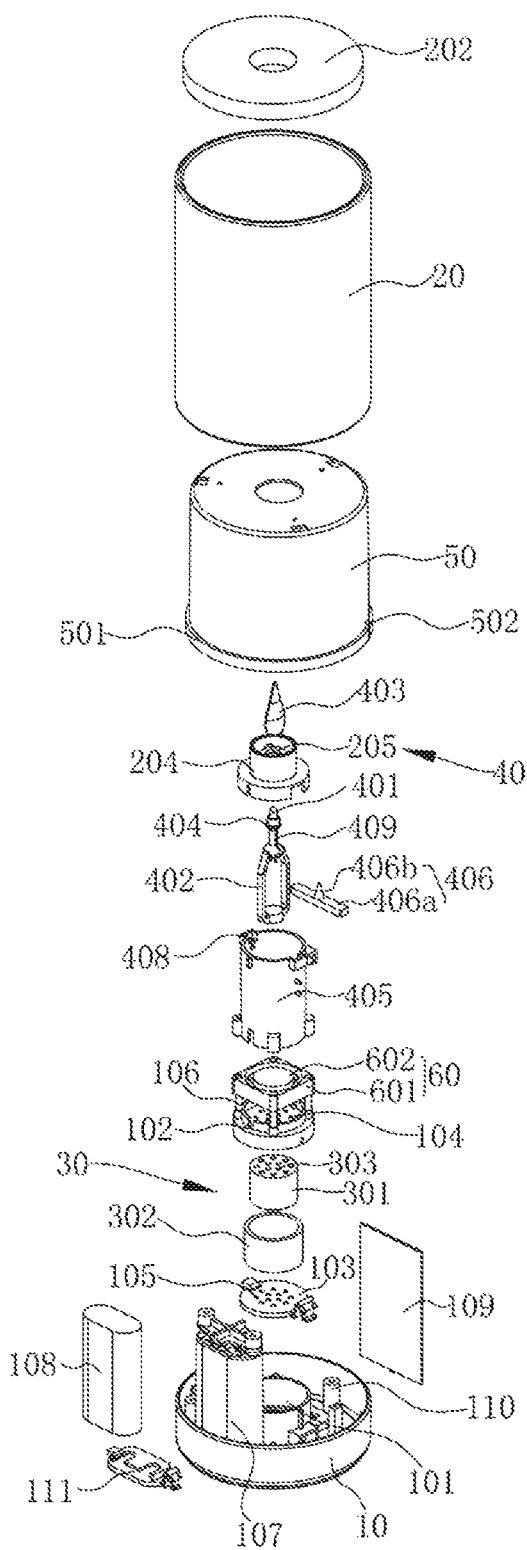
FIG. 3 is an exploded schematic view of an electric scented candle according to an embodiment of the present invention.

In the drawings, 10. base; 20. filled body; 30. fragrance assembly; 40. candle tip; 50. inner cover; 60. airflow generation device; 101. receiving cavity; 102. upper cap; 103. bottom cap; 104. first air holes; 105. second air holes; 106. connecting pins; 107. battery compartment; 108. battery; 109. circuit board; 110. first receiving holes; 111. battery cover; 112. third air holes; 113. indicator light; 201. holding plate; 202. layer of paraffin; 203. though-hole; 204. connecting element; 205. connecting hole; 301. solid perfume; 302. heating ring; 303. diffusing holes; 401. light source; 402. flame holder; 403. flame cover; 404. flame base; 405. fixing base; 406. swing support mechanism; 406a. fixing piece; 406b. cone-shaped supporting piece; 407. swing driving mechanism; 407a. magnet; 407b. electromagnetic coil; 408. mounting groove; 409. connecting rod; 501. flange; 502. engaging block; 601. housing; 602. air outlet body.

DETAILED DESCRIPTION OF ILLUSTRATED EMBODIMENTS

The invention will be further illustrated in the detailed description in conjunction with the drawings and the embodiments. The following embodiments are intended to illustrate the invention, but not to restrict the scope of the invention.

It should be understood that the terms, such as "up", "down", "left", and "right" as used in the description, refer to position and orientation relationships in accordance with drawings for convenience of description and for the purpose of simplicity. They are not intended to indicate or hint a limitation in terms of specific orientation or configuration and operation with specific orientation to the described device or element and should not be regarded as limiting.

Referring to FIGS. 1-4, in a preferred embodiment of the present invention, an electric scented candle comprises a base 10, a hollow filled body 20 having two ends respectively formed with an opening, a fragrance assembly 30, and a candle tip 40, wherein the lower end of the filled body 20 is detachably connected with the base 10, a holding plate 201 is arranged in the filled body 20, a layer of paraffin 202 is arranged on the upper side of the holding plate 201, the holding plate 201 is arranged adjacent to the upper opening of the filled body 20 and is provided with a though-hole 203, and the candle tip 40 is arranged in the filled body 20 and extends through the though-hole 203 to a position above the holding plate 201. Since the components including the candle tip 40 are all arranged in the filled body 20, the electric scented candle provides improved integration and achieves better aesthetics. The base 10 is provided with a receiving cavity 101 for accommodating the fragrance assembly 30, and the fragrance assembly 30 comprises a solid perfume 301 and a heating mechanism for heating the solid perfume 301. In the embodiment, the solid perfume 301 may be any of fragrant stick, fragrant slice, and fragrant bead, and fragrant stick is preferred.

In particular, since the fragrance assembly 30 is arranged in the receiving cavity 101 of the base 10 and comprises the solid perfume 301 and the heating mechanism for heating the solid perfume 301, the fragrance can be emitted uniformly due to the heating mechanism for heating the solid perfume 301. Due to the solid-state solid perfume 301, the volatilization of the solid perfume 301 can be significantly reduced to saves resources, and problems such as leakage of conventional essential oil can be avoided. Furthermore, since the base 10 is detachably connected with the filled body 20, it is convenient to replace the solid perfume 301 and maintain internal parts of the filled candle. Meanwhile, since the holding plate 201 is arranged in the filled body 20 and the candle tip 40 is arranged in the filled body 20 and extends through the though-hole 203 to a position above the holding plate 201, real burning flames can be simulated by the candle tip 40, and wax surface of real burning candles adjacent to the candle tip 40 can be simulated by the layer of paraffin 202 arranged on the holding plate 201, thereby providing better simulation effect of the scented candle.

In the embodiment, the filled body 20 is configured to have a hollow structure with two ends respectively formed with an opening, which subverts the design of the sealing bottom of conventional electric candles. Due to the non-sealed bottom of the filled body 20, an airflow path can be formed between the bottom of the filled body and the though-hole 203 of the holding plate 201 disposed at the top, to ensure air circulation and facilitate the diffusing of fragrance.

Figure 4:
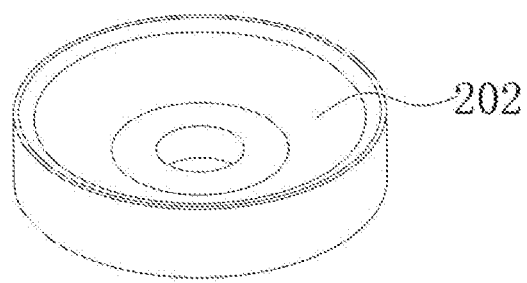
FIG. 4 is another schematic view illustrating a layer of paraffin according to an embodiment of the present invention.

To meet various requirements, the electric scented candle is arranged in such a manner that the upper side surface of the layer of paraffin 202 is aligned with the upper end surface of the filled body 20 or is recessed downwards along the filled body 20. In order to further improve simulation effect, the upper side surface of the layer of paraffin 202 may be formed as a planar surface, or a recessed surface, or a corrugated surface, to simulate various states of the wax surface during the burning of real candles. Referring to FIG. 4, the layer of paraffin 202 is formed to be recessed, to simulate the wax surface in a state in which the wax around the periphery of the candle tip 40 is melted during the burning of the candle tip 40.

In the embodiment, the filled body 20 may be oval shaped, straight cylinder shaped, trapezoid shaped, etc., to meet various requirements and provide aesthetics. The filled body 20 may be made of any of glass, plastic, paraffin, metal, and wood. Compared with conventional candles, the electric scented candle greatly reduces waste of paraffin resources.

Furthermore, the filled body 20 which is reusable provides aesthetics and saves resources. It should be noted that, since it is not necessary for the electric scented candle in the embodiment to physically burn, the filled body 20 may be made of paraffin, which improves simulation effect. Generally, the holding plate 201 and the filled body 20 may be integrally formed to facilitate a firm connection between the holding plate 201 and the filled body 20, thereby preventing the holding plate 201 from falling off. The base 10 may be mainly made of plastic and may be processed by surface treatments such as wood graining and electroplating, and preferably it may be made of glass in the embodiment. In the case that the filled body 20 is made of glass, the upper portion of the filled body 20 may be transparent or frosted, such that the flickering candlelight of the candle tip 40 is visible through the upper portion of the filled body 20, thereby achieving high entertainability of the electric scented candle.

Furthermore, the heating mechanism comprises a heating ring 302 arranged in the receiving cavity 101 and a first control circuit for controlling the heating of the heating ring 302, and the solid perfume 301 is arranged in the heating ring 302. By means of the heating ring 302, the solid perfume 301 can be evenly heated over 360 degrees, whereby the fragrance can be diffused uniformly. The first control circuit can be connected with a wireless device to achieve remote control in a wireless manner. Alternatively, in order to meet the requirements of producing fragrant vapors by means of the candle lamp in various applications, some specific heating modes may be set to perform continuous heating or intermittent heating. Preferably, the heating mechanism may further comprise a thermal insulation layer arranged between the inner wall of the receiving cavity 101 and the heating ring 302, for preventing, during the heating by means of the heating ring 302, the temperature of the receiving cavity 101 and also of the base 10 and the filled body 20 from being excessively high and influencing the operation of internal circuits and components and even of the whole filled candle.

In order to further increase the fragrance emitting efficiency and facilitate the diffusing of fragrance, the solid perfume 301 is provided with diffusing holes 303. When the solid perfume 301 is heated, fragrance can be emitted through its outer periphery and the diffusing holes 303, increasing fragrance emitting efficiency. Herein, the solid perfume 301 may be provided with one or more diffusing holes 303. In the case that a plurality of diffusing holes 303 are provided, the plurality of diffusing holes 303 may form honeycombed or quincunx arrangement on the solid perfume 301. Due to the detachable connection provided between the filled body 20 and the base 10 in the embodiment, the solid perfume 301, which may be directly arranged in the receiving cavity 101, may be of any type selected according to user requirements.

In the embodiment, an upper cap 102 is removably arranged at the upper end of the receiving cavity 101, and the upper cap 102 is provided with a plurality of first air holes 104, through which the fragrance emitted by the solid perfume 301 can pass through. Similarly, a bottom cap 103 may be removably arranged at the lower end of the receiving cavity 101, and the bottom cap 103 may be provided with a plurality of second air holes 105. The upper cap 102 and the bottom cap 103 may have dustproof function and serve to protect the solid perfume 301 and the heating ring 302 in the receiving cavity 101. The fragrance gas can pass through the first air holes 104 of the upper cap 102, through the space between the cover and caps, through the though-hole 203 of the holding plate 201, and then expelled from above. Also, it may be expelled through the second air holes 105 of the bottom cap 103. The bottom cap 103 may be formed as a grid plate. The solid perfume 301 may be put inside from above after opening the filled body 20 and also the upper cap 102, and alternatively, it may be put inside from below after opening the bottom cap 103, without opening the filled body 20, which facilitate operations for users and provides better adaptability of the filled candle, and the user can make selections freely according to the use environments or conditions. In the embodiment, third air holes 112 may be provided on the side wall of the base 10. The third air holes 112 are in communication with the interior of the filled body 20. Due to the third air holes 112, air convection with the fragrance gas inside the filled body 20 can be achieved to facilitate the diffusing of fragrance.

Preferably, an airflow generation device 60 for accelerating air circulation may be arranged above the receiving cavity 101. Due to the airflow generation device 60, the air flow can be accelerated to increase fragrance emitting efficiency. Generally, the airflow generation device 60 may be a fan, a blower, or the like. The airflow generation device 60 comprises a housing 601 and an air outlet body 602, and a plurality of connecting pins 106 are arranged at the upper end of the upper cap 102. By the connection between the housing 601 and the connecting pins 106, the airflow generation device 60 can be detachably connected with the upper cap 102. Due to the airflow generation device 60 arranged above the fragrance assembly 30, the airflow above the solid perfume 301 can be stirred up by the operation of the airflow generation device 60, thereby facilitating effective diffusing of the fragrance emitted by the solid perfume 301. In the embodiment, the electric scented candle may be configured with a plurality of fragrance diffusing modes. For example, the airflow generation device 60 may be actuated exclusively. In such case, even when the solid perfume 301 is not heated by means of the heating mechanism, the airflow generation device 60 may provide air circulation around the solid perfume 301 to facilitate the diffusing of the fragrance. Alternatively, the heating mechanism may be actuated exclusively and meanwhile the airflow generation device 60 is not actuated. In such case, the solid perfume can be heated by means of the heating mechanism, thereby facilitating the volatilization of the solid perfume and increasing the fragrance concentration around the solid perfume 301. In such case, the molecular movement facilitates the diffusing of the fragrance under such concentration difference. Alternatively, both the above can be combined. That is, the heating mechanism and the airflow generation device 60 can be simultaneously actuated to increase the fragrance diffusing efficiency.

In the embodiment, the candle tip 40 comprises a light source 401, a flame holder 402, a semitransparent flame cover 403, and a second control circuit for controlling the luminance and/or flicker frequency of the light source 401. Herein, the flame cover 403 is provided with a reflecting chamber, which usually has a cylinder shaped structure, such that the light reflected at each position of chamber can be uniformly distributed to ensure good use effect. The flame cover 403 may be drop shaped, or barrel shaped with varying diameters to simulate the profile of real flames. The upper end of the flame holder 402 extends through the though-hole 203 to a position above the holding plate 201 and is arranged with a flame base 404, the lower end of the flame cover 403 is connected with the flame base 404, the light source 401 is arranged in the flame base 404 in such a manner that the light emitted by the light source 401 can be projected through the reflecting chamber of the flame cover 403, to simulate real flames. The light source 401 and the flame cover 403 cooperated with each other take the place of the flame sheet and reflect light to simulate the flame light source 401. The second control circuit serves to control the luminance and/or flicker frequency of the light source 401. By means of the second control circuit, the luminance of the light source 401 can be controlled to simulate the flickering brightness of the flame, and the flicker frequency of the light source 401 can be controlled to simulate the swing motion of the flame. In this way, the realistic effect of the simulated flame is improved, and good use effect is ensured. Generally, the second control circuit and the light source 401 may be electrically connected in a wired or wireless manner. Preferably, the light source 401 may be one or more LED lamp beads. LED lamp beads have many characteristics such as low power consumption, high luminance, beautiful colors, vibration resistance, and a long lifetime. In the embodiment, the flame cover 403 may be semitransparent white cover or semi-transparent color cover.

In the embodiment, the base 10 is arranged with a battery compartment 107 for accommodating a battery 108, and the first control circuit, the second control circuit, and the light source 401 are electrically connected with the battery 108 which serves to supply power for the electric scented candle. It should be noted that, the battery 108 may be a rechargeable lithium battery, or a non-rechargeable battery, which is not specifically limited in the embodiment. In the embodiment, the first control circuit and the second control circuit are arranged on the circuit board 109, and the circuit board 109 is arranged on the base 10 and is disposed in the side portion of the receiving cavity 101. In this way, structural interference may be reduced. Since the heating of the solid perfume 301 and the light flashing or swing motion of the candle tip 40 are separately controlled by means of the first control circuit and the second control circuit respectively, the operation of emitting fragrance and the operation of the flame do not interfere with each other. Generally, the first control circuit and the second control circuit are respectively connected with a control switch. By means of different control switches, features and functions of the filled candle can be selected by the user. Preferably, an indicator light 113 may be arranged on the side wall of the base 10. The indicator light 113 can indicate operation mode of the filled candle intuitively and clearly. The indicator light 113 may be a bead having low luminance, which may not either interfere with sleep or result in light pollution. Generally, the battery compartment 107 is provided at its bottom with an opening through which the battery 108 may be put into the battery compartment 107 from below. A battery cover 111 may be movably arranged on the opening.

The electric scented candle further comprises an inner cover 50, the inner cover 50 is connected with the base 10 from above, and the filled body 20 covers the inner cover 50 from outside and is connected with the base 10. Due to the inner cover 50 which is arranged in the filled body 20 and in many cases made of opaque materials, the internal structure of the candle lamp can be covered and concealed such that the whole candle lamp can achieve better aesthetics. Generally, the base 10 is provided with a plurality of first receiving holes 110, the lower end of the inner cover 50 is provided with a plurality of second receiving holes, and the inner cover 50 and the base 10 can be connected and fixed by connecting elements respectively extending though the first receiving holes 110 and the second receiving holes. The connecting elements may be pins or screws. Furthermore, the inner cover 50 is provided at its lower end with a flange 501 extending outward, an engaging block 502 is arranged on the flange 501, and an engaging notch fitting with the engaging block 502 is arranged on the inner wall of the lower end of the filled body 20. In the case that the filled body 20 covers the flange 501 of the inner cover 50, the engaging block 502 can be engaged with the corresponding engaging notch to achieve retaining and fixing.

In the embodiment, the electric scented candle further comprises a fixing base 405, a swing support mechanism 406 arranged in the fixing base 405, and a swing driving mechanism 407 for driving the flame holder 402 to swing around the swing support mechanism 406, wherein the swing support mechanism 406 is arranged with a swing convex point, and the flame holder 402 is provided at its centre of gravity with a swing concave point by which it can be hung on the swing convex point. Due to the swing driving mechanism 407 for driving the flame holder 402 to swing around the swing support mechanism 406, the flame cover 403 can be driven to perform swing motion to simulate flickering burning flame. In this way, the realistic effect of the flame is improved, and good use effect is ensured. In the embodiment, the swing driving mechanism 407 comprises a magnet 407a arranged at the lower end of the flame holder 402 and an electromagnetic coil 407b arranged at the bottom of the fixing base 405, wherein the electromagnetic coil 407b is electrically connected with the second control circuit, the second control circuit is electrically connected with the circuit board 109, the magnet 407a is arranged at the lower end of the flame holder 402, and the electromagnetic coil 407b is arranged at the bottom of the fixing base 405, adjacent to the magnet 407a. In particular, by controlling the power on/off of the electromagnetic coil 407b and the direction of current by means of the second control circuit, attracting and repelling forces can be generated between the electromagnetic coil 407b and the magnet 407a. As the flame holder 402 is hung on the swing support mechanism 406 by the swing convex point, the flame holder 402 can perform regular swing motion in forward, backward, left and right directions around the swing convex point when an attracting or repelling force is applied on the magnet 407a. In this way, both the light source 401 disposed at the upper end of the flame holder 402 and the flame cover 403 can perform swing motion along with the flame holder 402, to simulate flickering effect of real burning flames. In this way, a stable swing motion can be realized, and it is easy to control. In particular, the fixing base 405 may be cylinder shaped, and the flame holder 402 is arranged in the fixing base 405. The swing support mechanism 406 may comprise a fixing piece 406a and a cone-shaped supporting piece 406b arranged on the fixing piece 406a, the swing convex point may be defined by the tip end of the cone-shaped supporting piece 406b, the top end of the fixing base 405 is arranged with a mounting groove 408, in which two ends of the fixing piece 406a are mounted, and the flame holder 402 is hung on the tip end of the cone-shaped supporting piece 406b by the swing concave point.

In the embodiment, in order to make sure the candle tip 40 is stable, a connecting element 204 is arranged in the though-hole 203 of the holding plate 201. The connecting element 204 is provided with a connecting hole 205 and comprises an abutment portion abutting on the lower side surface of the holding plate 201 and a connecting portion embedded in the though-hole 203, and the abutment portion has an inner diameter greater than that of the connecting portion. The upper end of the flame holder 402 is arranged with a connecting rod 409 which extends through the connecting hole 205 to a position above the connecting portion, and the flame base 404 is arranged at the top end of the connecting rod 409, such that both the flame base 404 and the flame cover 403 are arranged above the holding plate 201, thereby ensuring illumination effect of the light source 401.

Overall, embodiments of the present invention provides the electric scented candle, which comprises the base 10, the hollow filled body 20 having two ends respectively formed with the opening, the fragrance assembly 30 and the candle tip 40, wherein the fragrance assembly 30 is arranged in the receiving cavity 101 of the base 10. In particular, the fragrance assembly 30 comprises the solid perfume 301 and the heating mechanism for heating the solid perfume 301. By means of the heating mechanism for heating, the fragrance can be diffused uniformly. Due to the solid-state solid perfume 301, the volatilization of the solid perfume 301 can be effectively suppressed, thereby saving resources. Furthermore, since the base 10 is detachably connected with the filled body 20, it is convenient to replace the solid perfume 301 and maintain internal parts of the scented candle. Meanwhile, since the holding plate 201 is arranged in the filled body and the candle tip 40 is arranged in the filled body 20 and extends through the though-hole 203 to a position above the holding plate 201, real burning flames can be simulated by the candle tip 40, and wax surface of real burning candles adjacent to the candle tip 40 can be simulated by the layer of paraffin 202 arranged on the holding plate 201, thereby providing better simulation effect of the scented candle.

It should be understood that, in the present invention, terms such as "the first" and "the second" used herein for indicating various elements are merely intended to distinguish same type of elements from one another, but are not necessarily limited to these terms. For example, terms "the first" element may be referred to as "the second" element, and similarly, "the second" element may be referred to as "the first" element, without departing from the scope of the present invention.

The embodiments disclosed above are only preferred embodiments of the invention. It should be noted that for those skilled in the art, some improvements and alternatives can be made without departing from the principle of the invention, these improvements and alternatives should also be considered included within the scope of the invention.

The invention claimed is:

1. An electric scented candle, comprising a base, a hollow filled body having two ends respectively formed with an opening, a fragrance assembly, and a candle tip, wherein a lower end of the filled body is detachably connected with the base, a holding plate is arranged in the filled body, a layer of paraffin is arranged on an upper side of the holding plate, the holding plate is arranged adjacent to an upper opening of the filled body and is provided with a through-hole, and the candle tip is arranged in the filled body and extends through the through-hole to a position above the holding plate;
wherein the base is provided with a receiving cavity for accommodating the fragrance assembly, and the fragrance assembly comprises a solid perfume and a heating mechanism for heating the solid perfume;
wherein the heating mechanism comprises a heating ring arranged in the receiving cavity and a first control circuit for controlling heating of the heating ring, and the solid perfume is arranged in the heating ring;
wherein the heating mechanism comprises a thermal insulation layer arranged between an inner wall of the receiving cavity and the heating ring.

2. The electric scented candle according to claim 1, wherein the solid perfume is provided with a diffusing hole.

3. The electric scented candle according to claim 2, wherein the solid perfume is provided with a plurality of diffusing holes which form honeycombed or quincunx arrangement.

4. The electric scented candle according to claim 3, wherein the solid perfume is any of fragrant stick, fragrant slice, and fragrant bead.

5. The electric scented candle according to claim 4, wherein an upper cap is removably arranged at an upper end of the receiving cavity, and the upper cap is provided with a plurality of first air holes.

6. The electric scented candle according to claim 5, wherein an airflow generation device for accelerating air circulation is arranged above the receiving cavity.

7. The electric scented candle according to claim 6, wherein the airflow generation device comprises a housing and an air outlet body, a plurality of connecting pins are arranged at an upper end of the upper cap, and the housing is connected with the connecting pins.

8. The electric scented candle according to claim 5, wherein a bottom cap is removably arranged at a lower end of the receiving cavity, and the bottom cap is provided with a plurality of second air holes.

9. The electric scented candle according to claim 5, wherein a plurality of third air holes in communication with an interior of the filled body are provided on a side wall of the base.

10. The electric scented candle according to claim 1, wherein the candle tip comprises a light source, a flame holder, a semitransparent flame cover, and a second control circuit for controlling luminance and/or flicker frequency of the light source, wherein an upper end of the flame holder extends through the through-hole to a position above the holding plate and is arranged with a flame base, a lower end of the flame cover is connected with the flame base, the light source is arranged in the flame base in such a manner that a light emitted by the light source can be projected through a reflecting chamber of the flame cover.

11. The electric scented candle according to claim 10, wherein the electric scented candle comprises an inner cover, the inner cover is connected with the base from above, and the filled body covers the inner cover from outside and is connected with the base.

12. The electric scented candle according to claim 10, wherein the electric scented candle comprises a fixing base, a swing support mechanism arranged in the fixing base, and a swing driving mechanism for driving the flame holder to swing around the swing support mechanism, wherein the swing support mechanism is arranged with a swing convex point, the flame holder is provided at its centre of gravity with a swing concave point by which it can be hung on the swing convex point, and the swing driving mechanism comprises a magnet arranged at a lower end of the flame holder and an electromagnetic coil arranged at a bottom of the fixing base.

13. The electric scented candle according to claim 1, wherein the holding plate and the filled body are integrally formed, and the filled body is made of any of glass, plastic, paraffin, metal, and wood.

14. The electric scented candle according to claim 13, wherein the filled body is oval shaped, straight cylinder shaped, or trapezoid shaped.

15. The electric scented candle according to claim 1, wherein an upper side surface of the layer of paraffin is aligned with an upper end surface of the filled body or is recessed downwards along the filled body.

16. The electric scented candle according to claim 1, wherein an upper side surface of the layer of paraffin is formed as a planar surface, or a recessed surface, or a corrugated surface.

17. The electric scented candle according to claim 1, wherein the base is arranged with a battery compartment for accommodating a battery.

18. The electric scented candle according to claim 1, wherein an indicator light is arranged on a side wall of the base.

\* \* \* \* \*